(12) United States Patent
Altshuler

(10) Patent No.: US 6,558,372 B1
(45) Date of Patent: *May 6, 2003

(54) METHOD FOR TREATING MATERIALS, ESPECIALLY BIOLOGICAL TISSUES, USING LIGHT INDUCTION AND DEVICE FOR REALIZING THE SAME

(75) Inventor: Gregory Altshuler, Wilmington, MA (US)

(73) Assignee: Gregory B. Altshuler, Wilmington, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/381,773
(22) PCT Filed: Jan. 19, 1999
(86) PCT No.: PCT/RU99/00016
§ 371 (c)(1),
(2), (4) Date: May 16, 2000
(87) PCT Pub. No.: WO99/37363
PCT Pub. Date: Jul. 29, 1999

(30) Foreign Application Priority Data

Jan. 23, 1998 (RU) .......................................... 98102083

(51) Int. Cl.⁷ ............................................... A61B 18/18
(52) U.S. Cl. ............................... 606/2; 606/10; 606/13; 607/88; 128/898; 433/29; 433/215
(58) Field of Search .................. 606/10, 13, 16, 606/22, 127, 128, 2; 433/29, 215; 128/898; 607/88–92

(56) References Cited

U.S. PATENT DOCUMENTS 4,503,853 A    3/1985    Ota et al.
5,020,995 A    6/1991    Levy (List continued on next page.)

FOREIGN PATENT DOCUMENTS

| EP | 0 976 421 A1 | 2/2000 |
| SU | 1593669 A | 9/1990 |
| WO | 00-62694 A1 | 10/2000 |

OTHER PUBLICATIONS

G.B. Altshuler, "Human tooth in low and high intensive light fields," Proc. SPIE, vol. 2623, pp. 68–81, 1996, St. Petersburg State Institute of Fine Mechanics & Optics, Department of Quantum Electronics & Biomedical Optics.

M.L. Wolbarsht, "Laser Applications in Medicine and Biology," vol. 1, pp. 1–63, Plenum Press, New York—London, 1971.

(List continued on next page.)

*Primary Examiner*—Linda C. M. Dvorak
*Assistant Examiner*—Ahmed M Farah
(74) *Attorney, Agent, or Firm*—Wolf, Greenfield & Sacks, P.C.

(57) ABSTRACT

A method and apparatus are provided for processing biological tissue and other materials which involves providing or distributing a substance containing abrasive particles to an area in front of at least a portion of a surface of the material and irradiating both the substance and the portion of the surface with light from a selected source, the light being selected and delivered in a manner such that selective ablation is caused on the substance sufficient to force the abrasive particles under a selected pulse against the portion of the surface. Ablation may be of the particles themselves or the particles may be contained within a shell, with ablation being of the shell. The substance is preferably delivered as a series of distribution pulses with the light being delivered either continuously or as light pulses having a predetermined relationship to the distribution pulses.

44 Claims, 4 Drawing Sheets

OTHER PUBLICATIONS

| | | | |
|---|---|---|---|
| 5,060,527 A | | 10/1991 | Burgess |
| 5,199,870 A | | 4/1993 | Steiner et al. |
| 5,257,935 A | | 11/1993 | Vassiliadis et al. |
| 5,267,856 A | | 12/1993 | Wolbarsht et al. |
| 5,334,016 A | * | 8/1994 | Goldsmith et al. ............ 433/29 |
| 5,401,171 A | | 3/1995 | Paghdiwala |
| 5,409,376 A | * | 4/1995 | Murphy ........................ 433/29 |
| 5,554,029 A | * | 9/1996 | Kowalyk et al. ............ 433/215 |
| 5,636,983 A | * | 6/1997 | Shoji et al. .................... 433/29 |
| 5,734,765 A | | 3/1998 | Artjushenko et al. |
| 5,746,596 A | * | 5/1998 | Gallant et al. ................. 433/88 |
| 5,752,948 A | * | 5/1998 | Tankovich et al. ............. 606/9 |
| 5,785,703 A | | 7/1998 | Goodman et al. |
| 5,800,165 A | * | 9/1998 | Kirsch et al. ................. 433/29 |
| 5,873,875 A | * | 2/1999 | Altshuler ..................... 606/10 |
| 5,968,035 A | * | 10/1999 | Goodman et al. ............. 606/12 |
| 6,083,218 A | * | 7/2000 | Chou ........................... 606/10 |
| 6,137,110 A | | 10/2000 | Pellin et al. |
| 6,162,055 A | * | 12/2000 | Montgomery et al. ...... 433/216 |
| 6,270,342 B1 | * | 8/2001 | Neuberger et al. ............ 433/29 |

OTHER PUBLICATIONS

Leon Goldman, MD, R. James Rockwell, MS, Robert Meyers, Robert Otten, Robert G. Wilson, MD, and K. William Kitzmiller, MD, "Laser Treatment of Tattoos," JAMA, Sep. 11, 1967.

Leonard H. Finkelstein and Lee M. Blatstein, "Epilation of Hair–Bearing Urethral Grafts Using The Neodymium: Yag Surgical Laser," The Journal of Urology, vol. 146, pp. 840–842.

Janet Morgan, James E. Whitaker and Allan R. Oseroff, "GRP78 Induction by Calcium Ionophore Potentiates Photodynamic Therapy Using the Mitochondrial Targeting Dye Victoria Blue BO," Photochemistry and Photobiology, 1998, 67(1): 155–164.

* cited by examiner

METHOD FOR TREATING MATERIALS, ESPECIALLY BIOLOGICAL TISSUES, USING LIGHT INDUCTION AND DEVICE FOR REALIZING THE SAME

FIELD OF THE INVENTION

The invention concerns the processing of materials and medical engineering and can be used for the processing of materials in dentistry, orthopedics, surgery, dermatology and other fields of medicine, for removal and destruction of hard and soft materials and tissues and for modification of properties of hard and soft materials and tissue surfaces.

BACKGROUND OF THE INVENTION

The processing of hard dental tissues by simultaneous influence of laser radiation and the flow of abrasive particle is shown in U.S. Pat. No. 5,334,016, where a pneumatic system forms an air jet saturated by abrasive material and directs it on an object inside a patient's mount. A disadvantage of this method is the necessity of delivering the abrasive particles through a pipe at very high speed, this causing loss of essential energy by the particles. Therefore, near the tissues, there are particles with kinetic energies that differ considerably, so that only some of them participate in the removal of tissues, enamel and dentin and the remaining particles are stored in the patient's mouth, producing no useful effect. It can also be difficult to completely remove these particles, even with the help of an additional aspiration system.

The application of laser radiation in this prior art method results in a negligible increase in efficiency, since the air-abrasive flow and laser radiation do not interact, but independently produce additive influence so that the efficiency of laser processing is limited by the finite value of reflection and absorption indices of tissues. The removal, cutting, drilling and other specific methods of laser-tissue interaction are also accompanied in a number of cases with increased necrosis.

Another prior art method and apparatus for processing of materials including tissues uses particles of condensed substance (drops of liquid), which acceleration in the direction of a surface of the material being processed as a result of interaction with electromagnetic radiation directed to the processed surface. The main disadvantage of this technique is the insufficient hardness of liquid particles, so that, even at high speed, they cannot cut most materials, particularly hard materials such as metals, ceramics, enamel or dentin of tooth, with high efficiency.

A need therefore exists for methods and apparatus for the improved utilizing of both radiation and particles in the efficient and accurate processing of materials, including tissues.

SUMMARY OF THE INVENTION

In accordance with the above, this invention provides a method for processing a material having an outer surface, the term "material" as used herein including biological tissue, and biological tissue being the material on which the invention is primarily adapted for use. However, the invention is by no means limited to use on biological tissue. The method includes distributing a substance containing abrasive particles in an area in front of at least a portion of the surface and irradiating both the substance and the portion of the surface with light selected to cause selective ablation of the substance sufficient to force the abrasion particles under a selected pulse against the portion of the surface. For some embodiments of the invention, the substance is the abrasive particles, the particles being of a size to be selectively ablated by the irradiation to force the particles against the surface. For this embodiment, the particles should have a size $d \gg k^{-1}(\lambda)$, d, the characteristic size of particle, being between 1 and 1000 $\mu$m and k($\lambda$), the absorption index of the particle material at wavelength $\lambda$, being between $10^5$ cm$^{-1}$ and $10^2$ cm$^{-1}$. These particles may for example be distributed into the area in front of the surface by airflow.

Alternatively, the substance may include the particles, each enclosed within a shell, the selective ablation being of the shell. For this embodiment, each shell should have a thickness $\delta$ such that $\delta \gg k^{-1}(\lambda)$. For this embodiment, it is also preferable that $1 < \delta < 1000$ $\mu$m and that $10^5$ cm$^{-1}>k>10^2$ cm$^{-1}$. The substance may be a suspension of the particles in a liquid, the liquid being selectively ablated by the light. The distributing step distributes the suspension to the surface to cool the material and the irradiating step irradiates a small portion of the surface, particles being forced for the most part only against such small portion to cause the processing thereof. The shell may be substantially completely ablated by the irradiation thereof so as not to interfere with the action of the particles on the surface.

For still another embodiment of the invention, the substance is a substantially solid body containing the particles, a component of the body being selectively ablated by the light, and the distributing step includes the step performed throughout the processing of the material of maintaining a portion of the body between the light and the portion of the surface being processed. The solid body may be formed as a suspension of the particles in a substantially solid binder, the binder for example being the component selectively ablated by the light, or the solid body may be formed of the particles processed, for example by sintering or under pressure to adhere in the desired shape.

The substance may be distributed to the area in front of the surface for a duration $\tau$, the light having an energy density E near the surface such that $\tau \ll d^2/4\alpha$ and $E \gg k^{-1}(\lambda)\rho Q$. E may be, for example, between $10^{-1}$ and $10^4$ j/cm$^2$.

The irradiation may be performed continuously or may be performed as a sequence of time-spaced light pulses. Similarly, the distribution of substance may be by a series of distribution pulses. The distribution pulses may be synchronized with the light pulses or may occur before each light pulse, the duration of the distribution pulses being less than the time between light pulses in the latter case. A distribution pulses may also have a repetition rate which is less than that for the light pulses.

The invention also includes apparatus for processing a material, as previously defined, having an outer surface, which apparatus includes a mechanism selectively providing a substance containing abrasive particles in an area in front of at least a portion of the surface to be processed, a light source, and a system for selectively directing light from the source to irradiate both the substance and the portion of the surface, the source and the system being selected to cause selective ablation of the substance in response to irradiation thereof sufficient to force abrasive particles under a selected pulse against the portion of the surface. The light source may for example be a laser, an incandescent lamp or a flash lamp. The system for selectively directing light may include a control which operates the source in a selected pulse mode and an optical system directing light from the source to a tip, the mechanism selectively providing the substance through the tip to the area and the tip being adapted to direct light through the area to the portion of the surface. The substance may also be provided to the area by the mechanism as a series of distribution pulses. The distribution pulses may be provided in synchronism with the light pulses from the source or the distribution pulses may occur before each light pulse, the duration of the distribution pulses being less than the time between light pulses. The distribution pulses may have a repetition rate which is less than the repetition rate for the selected pulse mode in which the source is operated. Alternatively, the control may operate the source continuously.

The mechanism may be operated to distribute the substance to the area for a duration τ, and the source may deliver light radiation having an energy density E near the surface of the material such that $10^{-1} < E < 10^4$ j/cm². In this case, E is preferably between $10^{-1}$ and $10^4$ j/cm².

For some embodiments, the substance is the abrasive particles and the mechanism includes a source of the particles, a carrier for delivering the particles to the area, and a control for operating on at least one of the carrier and the source to provide a controlled delivery of particles to the area, the particles being of a size to be selectively ablated by light irradiation directed thereat from the source. The carrier may be delivered under pressure to an air pipe under control of a valve operated by the control, the particles being delivered from a source thereof to the air pipe to be carried therethrough by air to the area in front of the material surface. Alternatively, the carrier may be a liquid, the substance being a suspension of the particles in the liquid, the liquid being selectively ablated by the light. In this case, particularly where the material is biological tissue, the mechanism may be controlled to deliver the suspension to the surface to cool the material prior to the system applying light to the substance to ablate the liquid, forcing the particles for the most part only against a small portion of the surface irradiated by the light to cause processing of material at the portion.

For some embodiments of the invention, the substance is in the form of a substantially solid body containing the particles, an indexing mechanism being provided for both supporting and maintaining the body in an area between the light and the portion of the surface to be processed. The solid body may be a suspension of the particles in a substantially solid binder, the binder for example being selectively ablated by the light, or the particles may be processed to adhere in a desired shape, for example by sintering, pressure or the like.

The substance may be sapphire particles suspended in water, with a light source for such substance being, for example, an ER-laser. Where a laser is used as the light source, the light source may for example be $CO_2$ laser or an excimer laser. For one embodiment, a neodymium laser is used with carbon particles as the substance. Where the material being processed is biological tissue, the particles are preferably biologically safe materials such as hydroxyapatite, carbon, silicon or ice.

The foregoing and other objects, features and advantages of the invention will be apparent from the following more detailed description of preferred embodiments as illustrated in the accompanying drawings, the same reference numerals being used for common elements in all the drawings.

IN THE DRAWINGS

DETAILED DESCRIPTION

Figure 1A:
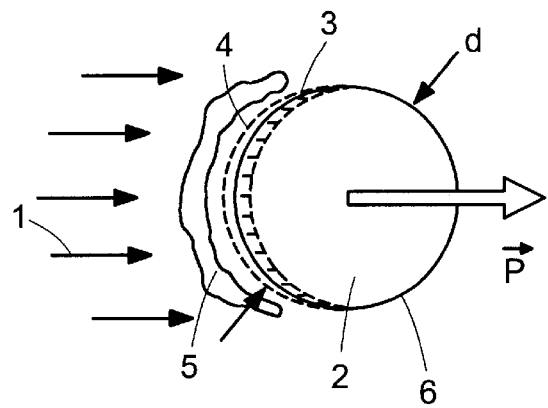
FIGS. 1a–1c are diagrammatic representations of a particle showing the principle of conversion of light energy into mechanical energy of the particles for three different types of particles.

FIG. 1a illustrates the principle of conversion of laser beam or other light energy into mechanical energy of abrasive particles. Light flow or radiation 1 at a wavelength λ falls on an abrasive particle 2. While the form of the particle is arbitrary, for simplicity it will be assumed to be a sphere. The wavelength of light flow 1 and the size and material of abrasive particle 2 are selected so that the conditions $d >> k^{-1}(\lambda)$ are satisfied, where d is a characteristic size of a particle 2, and k(λ) is the absorption index of the particle material at wavelength λ. In this case, the depth of light penetration into particle 2 will be less than its size. That is a necessary condition, together with the limitation of exposure duration to provide heating of only a part of the abrasive particle. The duration τ and the energy density E of an exposure of particles satisfy the following conditions:

$$\tau << d^2/4\alpha$$

$$E >> k^{-1}(\lambda)\rho Q$$

where:
α=index of temperature conductivity for the material of abrasive particle 2,
ρ=density of the material of abrasive particle 2,
Q=specific energy of transition of the material of abrasive particle 2 from solid to gaseous state.

The first condition means that heating of the surface of particle 2 which is turned to the source of light radiation 1 takes place adiabatically and does not result in the uniform heating of the whole particle. The second condition means that the energy absorbed by a part 3 of the particle 2 adjacent the surface turned to light radiation 1 is sufficient for evaporation (ablation) of this part. Thus, when these conditions are realized, a part 4 of particle 2 (part 3 after ablation) is vaporized and saturated steam 5, produced due to ablation of part 4, transfers a mechanical pulse P of jet recoil to the non-vaporized part 6 of particle 2, accelerating part 6 of the abrasive particle in the direction of light propagation.

Figure 1B:
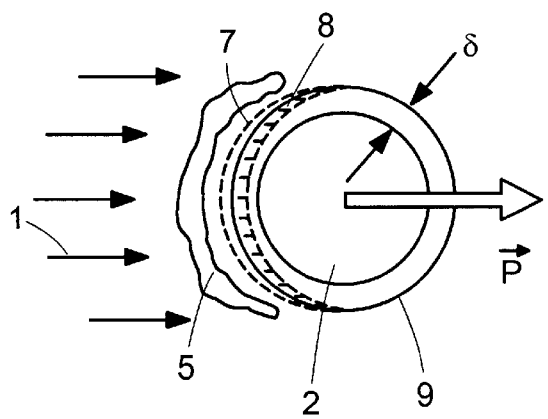

Similarly, referring to FIG. 1b, for the abrasive particle 2 inside a shell 9, the mechanism of conversion of light energy into mechanical energy of the abrasive particle involves ablation of a part 7 of the heated area 8 of shell 9. Shell 9 is formed from a material with absorption index k(λ) which satisfies to the condition $\delta >> k^{-1}(\lambda)$, where δ=thickness of shell 9.

The material of shell 9 may be a hard inorganic or polymeric; it can also be doped by ions or molecules which strongly absorb the optical radiation. The shell may also be a liquid layer. If the liquid strongly absorbs light radiation at wavelength λ, the conversion of energy is provided due to ablation of the liquid. The shell may be partially ablated, or may be fully ablated so as not to interfere with passage of and/or processing by the particles.

Figure 1C:
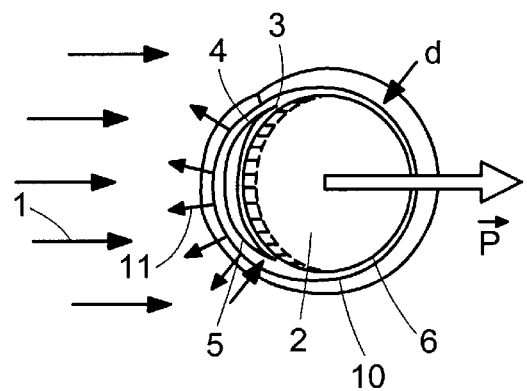

If the shell is transparent to the light radiation, the mechanism of conversion of light energy into mechanical energy of a particle is illustrated by FIG. 1c. The light flow 1 causes the ablation of a part 4 of a particle 2 resulting in saturated steam 5 swelling transparent shell 10 and ultimately tearing it. Since in the beginning, the evaporation takes place in a volume closed by shell 10, the pressure of saturated steam 5 reaches a value considerably greater than in the case when there is no transparent shell, resulting in an increased jet pulse. Saturated steam 5 pulled out under shell 10, together with breakdown products 11, transfers the mechanical pulse P to non-vaporized part 6 of particle 2.

The duration τ and the energy density E of exposure in the case of an absorbing shell 9 as shown in FIG. 1b should satisfy to the conditions:

$$\tau << \delta^2 / 4\alpha$$

$$E >> k^{-1}(\lambda) \rho Q$$

where,
- α=index of temperature conductivity of the material of shell 9;
- ρ=density of the material of shell 9;
- Q=specific energy of transition of the material of absorbing shell 9 from solid to gaseous state.

Thus, due to jet recoil arising because of asymmetric evaporation of material of an abrasive particle or its shell, the abrasive particle gets a mechanical pulse $\vec{P}_1$ which, being added to an initial pulse drive $\vec{P}_0$ applied to the abrasive particle, yields a total pulse $\vec{P}$ applied to the particle $$\vec{P} = \vec{P}_1 + \vec{P}_0$$

For preferred embodiments, the initial pulse of abrasive particles is negligibly low in comparison with $\vec{P}_1$; therefore in practice $\vec{P} = \vec{P}_1$ and the direction of $\vec{P}$ substantially coincides with the direction of light radiation.

It is known that the interaction of abrasive particles with a material surface under low values of pulses and energies results in the hardening or other modification of the material surface, and that, under strong pulses and energies, removal or cutting of the material surface is observed. The efficiency of these processes depends on the ratio of microhardness of the abrasive particles exceeding the microhardness of the processed material. Universal abrasive particles include particles of diamond and/or sapphire which have hardnesses exceeding the hardness of most other materials. Where the material being processed is tissue, the material(s) for the abrasive particles are preferably biologically safe materials, for example hydroxyapatite, carbon, silicon, ice and other materials.

The size of the abrasive particles and/or their shells should satisfy the above conditions; but in any case, the size of the abrasive particles and/or the thickness of the absorbing shell should be more than the radiation wavelength in order to provide the asymmetric irradiation. Taking into account the optical range of wavelengths, the size of the abrasive particles or absorbing shell should not be less than one micrometer. However, it is necessary that the size of an abrasive particle be less than the transversal size of the light flow or beam 1 in the field of their intersection (i.e., it should not be more than 1 millimeter).

The index of absorption of the material for particles 2 or shell 9 for dimensions according to the above formulas should be $10^2$–$10^5$ cm$^{-1}$. The duration of exposure can be within the range $10^{-15}$–$10^{-1}$ s, and the energy density of exposure can be within the range $10^{-1}$–$10^4$ J/cm$^2$.

Figure 2A:
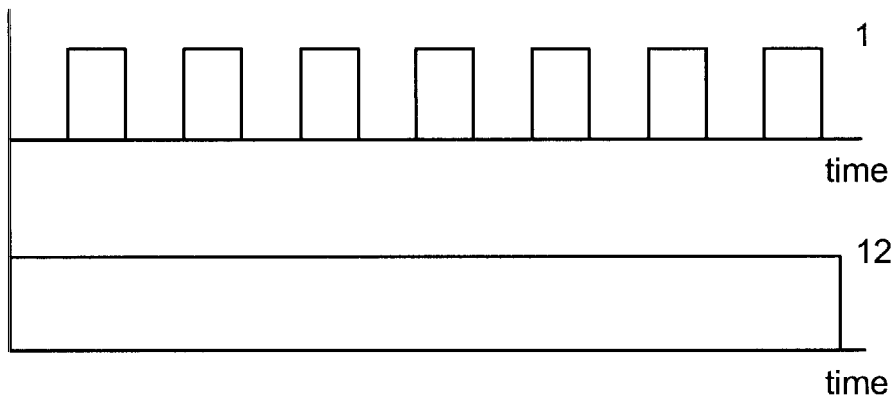
FIGS. 2a–2e are temporal diagrams of light and abrasive flow for various embodiments of the invention.
Figure 2B:
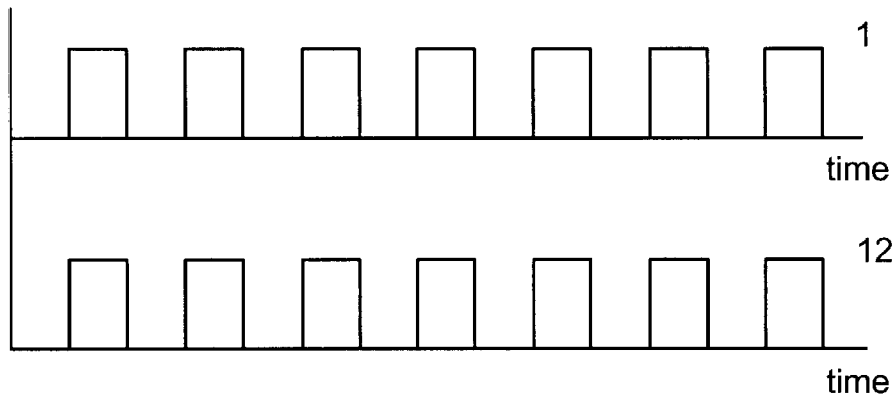
Figure 2C:
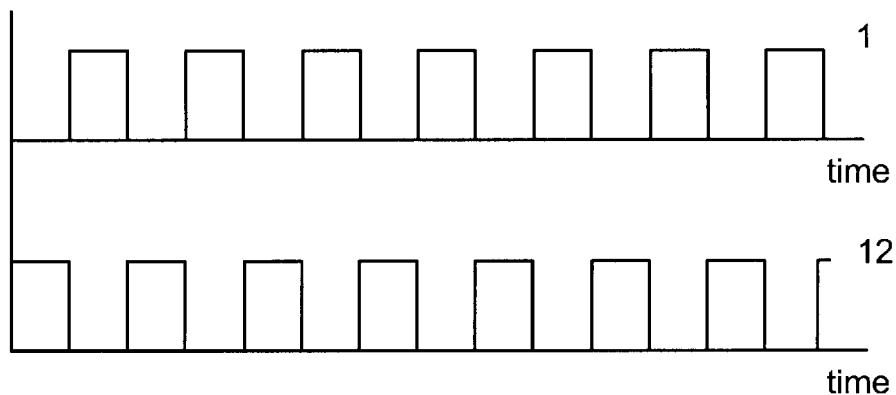

The realization of the method of this invention is possible if several temporal operation modes are observed. In the first case (FIG. 2a), the light flow 1 is represented by light pulses having a selected repetition rate and the flow 12 of abrasive particle 2 is continuous. This mode is simplest and cheapest. However, in this case it is possible that the accumulation of waste particles may obstruct the effective utilization of light energy in the zone of processing. The same result is possible under application of continuous light and abrasive flow. In the second and third modes (FIGS. 2b and 2c), light flow 1 and flow 12 of abrasive particles 2 are both pulsed. In these modes, the repetition rates of particle and light pulses are equal. In the second mode (FIG. 2b), the light and particle pulses are superimposed. By regulation of the pulse duration of flow 12, it is possible to precisely set the consumption of abrasive particles, and to also avoid the formation of a layer of abrasive particles on the material surface being processed. Where tissue is the material being processed, it is possible to reduce the invasiveness of the procedure by lowering the energy of light flow 1 directly interacting with tissue. In this case, the light pulses only accelerate the abrasive particles, removal, cutting or modification of material taking place only as a result of the collision of abrasive particles with the tissues because of fragile or viscous cracking, and also due to elastic impact extrusion.

Figure 2D:
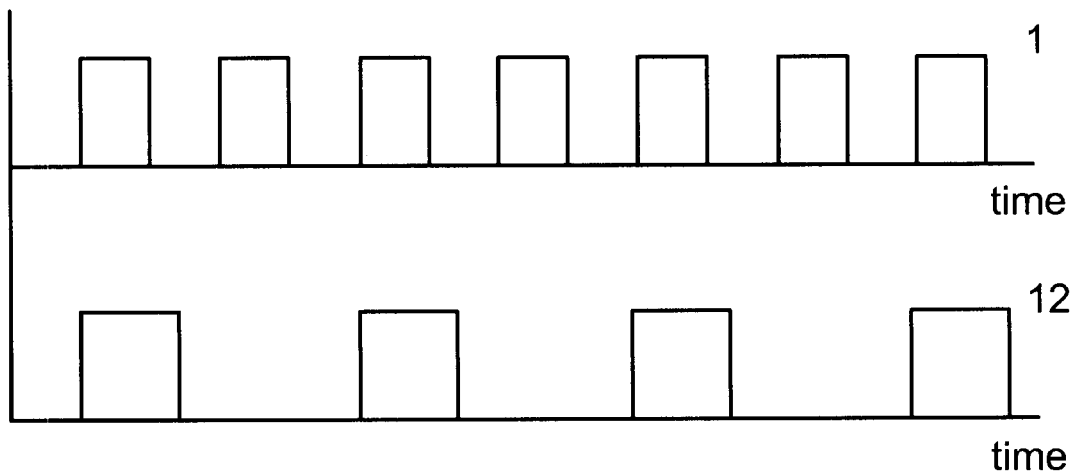
Figure 2E:
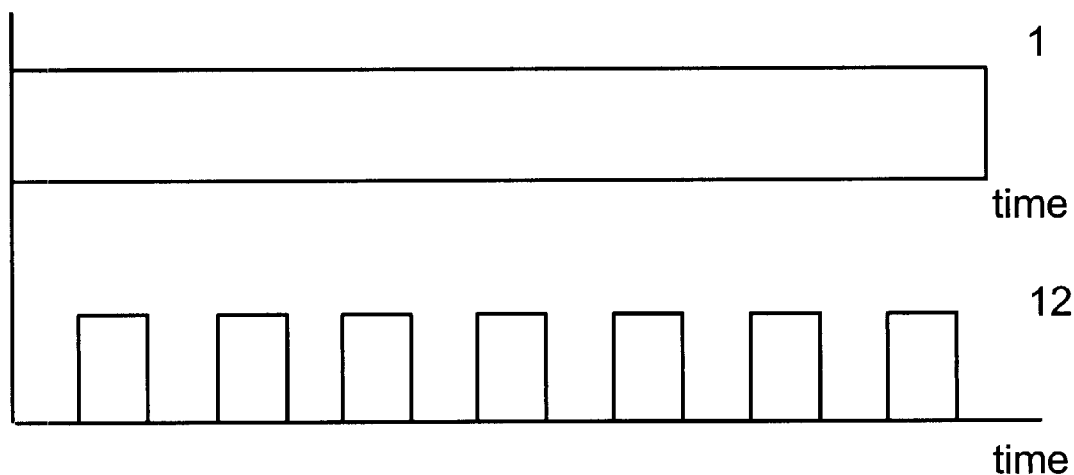

In the third mode (FIG. 2c), each pulse of particle flow 12 precedes the corresponding pulse of light flow 1. In this case a lamina of abrasive particles is formed on the surface of the material before the arrival of the light pulse, and removal, cutting or modification of the material is produced by direct transfer of a jet recoil pulse of an abrasive particle resulting from ablation and evaporation of parts of the abrasive particles or their shells. For the fourth operation mode (FIG. 2d), the repetition rate of light pulses 1 is greater than the repetition rate of the flow 12 of abrasive particles, but the duration of each light pulse is shorter then that of each particle pulse. In this case, a number of the light pulses affect the material together with abrasive particle pulses and the rest of the light pulses influence the material directly. Such a mode can be useful when the light influence differs essentially from the abrasive one and can itself be useful for material processing. For example, for an illustrative embodiment, the cutting of soft tissue takes place under the combined influence and the coagulation of blood vessels occurs under the influence of light pulses. The same result is achieved under continuous irradiation and pulsed flow of particles (FIG. 2e).

A device for realization of the proposed method will now be described. It comprises a source of optical light radiation, a control unit, a power supply for the source, an optical system for delivering radiation to a zone of processing of the material being processed, a tank with abrasive particles and a mechanism which delivers abrasive particles to the zone of processing. The mechanism for delivering abrasive particles includes a valve connected to an output of the control unit. Another output of the control unit is connected to an input of the power supply. The radiation delivery system can be made as an optically conjugated lens, an optical fiber and a mirror. The delivery mechanism for abrasive particles is, in the simplest case, represented by an airpipe connected to an air compressor and a tank with abrasive particles. Alternatively, the tank can be connected to a tank with liquid, particles flowing with the liquid from the tank through the pipe leading to the zone of processing. The tanks can be joint, in which case a liquid suspension of abrasive particles from the joint tank is supplied to the zone of processing through the pipe. The valve is preferably an electromechanical switch and is located on an output to the airpipe from the air compressor. The tank is connected to a pump. The outputs of the airpipe and the pipe, together with an output of the optical system delivering radiation to the zone of processing of the material, are joined in a tip containing the outputs from the optical system, the airpipe and the pipe respectively (See FIGS. 3a–3a).

In operation, radiation from the optical source 13 is delivered to zone of processing 17 of a material through radiation delivery system 16. The flow of abrasive particles 2 is delivered to the same zone from mechanism 19 in the form of a flow of abrasive particles in gas or in liquid stream through airpipe 24 and/or pipe 27. The light flow 1 and the abrasive flow 12 intersect in the zone of processing. Under this condition, light flow 1 causes the ablation of abrasive particles 2 which transfers the mechanical pulse obtained as indicated above to the surface of the processed material in zone 17, producing the elastic implantation or cracking. If a liquid-abrasive flow is used, the role of the liquid consists additionally in the cooling of the processed material in zone 17 and preventing its overheating. The light flow can also affect directly on the processed material, producing its ablation or selective heating. Control unit 14 regulates operation of the device by controlling its main parameters; namely, energy of optical radiation and consumption of abrasive material. Control unit 14 may also control the processing mode (FIGS. 2a–2e). Abrasive flow 12 may for example be represented as a pulse having a duration and synchronization with respect to the light pulse which controls the processing mode. While in the discussion above, it has been assumed that it is the particle being ablated, the light being at a wavelength for which the liquid carrier, for example water, is transparent, the wavelength of light and the liquid carrier can be selected such that the carrier functions as a FIG. 1b shell, being ablated by the light to propel the particles. A transparent carrier may result in operation as per FIGS. 1a and/or 1c.

Figure 3A:
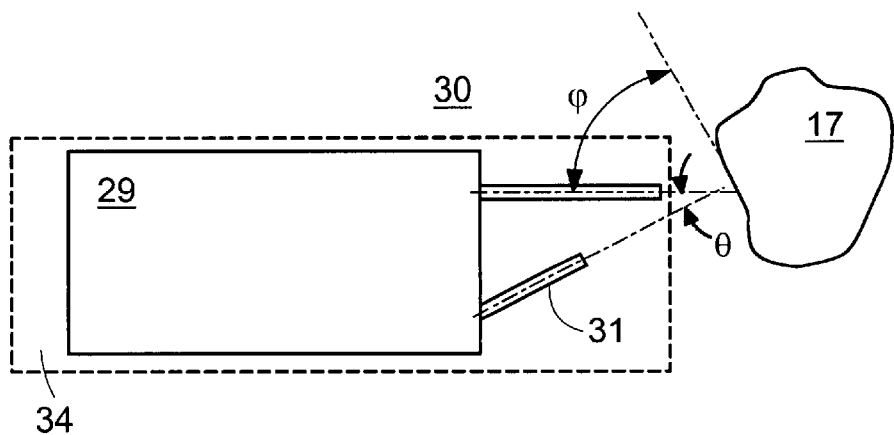
FIGS. 3a–3c are schematic representations of one aspect of the present invention.
Figure 3B:
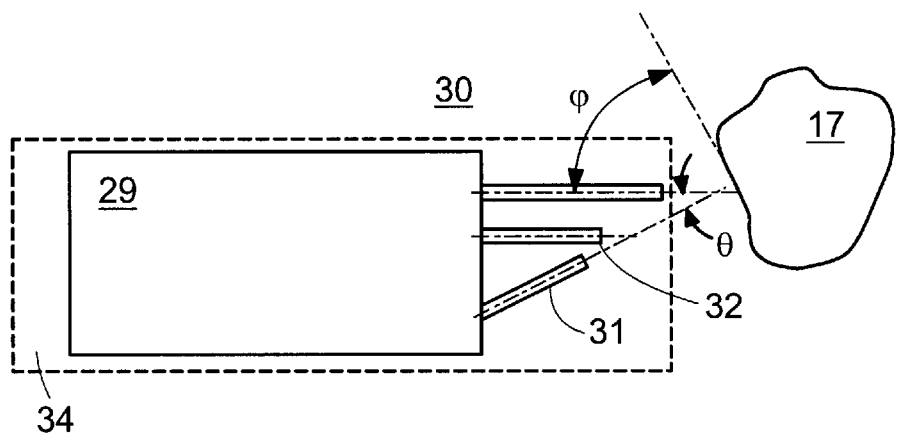
Figure 3C:
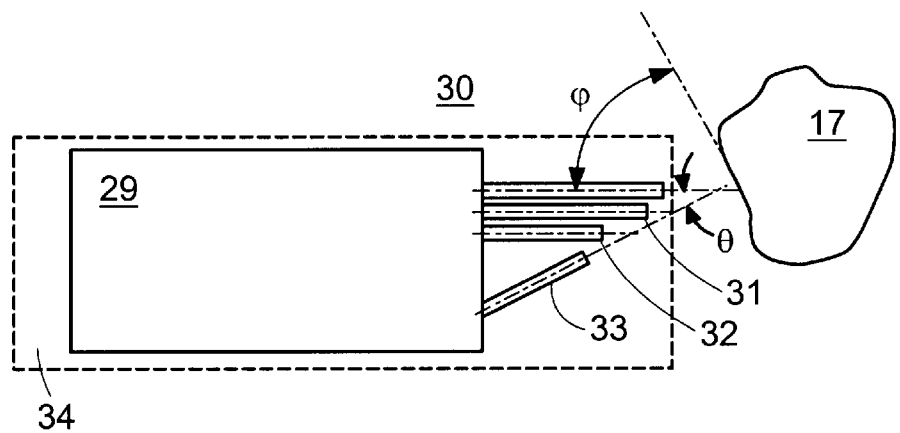

Various versions of the device tip 29 are shown in FIGS. 3a–3c. The tip with light output 30 and air-abrasive output 31 is shown in FIG. 3a. The light output 30 is for example an optical fiber. The light radiation is directed on processed material zone 17, in this case by the optical fiber 30 at an angle φ. The tip 29 is oriented as a whole to the surface of processed material zone 17 so that the angle φ between the axis of the light beam and the perpendicular to the surface of material zone 17 has a predetermined value. The axis of flow 12 of abrasive particles 2 emitted from the air-abrasive output 31 is directed at an angle θ to the axis of light flow 1. This angle is equal to φ under the perpendicular incidence of the flow 12. By changing the φ and θ, it is possible to control the efficiency of material removal and the microcontour of the processed surface.

FIG. 3b illustrates a tip 29 where the liquid-abrasive flow is supplied under low pressure through the nozzle 32 toward one 17, but is taken before reaching zone 17 in a gas jet directed by nozzle 31 to the area of intersection with light flow 1. As discussed earlier, the further direction of abrasive particle motion coincides with the direction of light flow.

FIG. 3c shows a version of tip 29 in which, besides the light output 30, air abrasive output 31 and output for liquid abrasive 32, there is an extra output 33 for air. In this case, the air-abrasive jet is supplied through the output 31 under low pressure, and the flow of liquid supplied through the nozzle 32 is taken by high pressure air flow from the nozzle 33 in the direction of the irradiated zone. All parts of each tip are assembled inside a housing 34. In addition to the tip configuration shown in FIGS. 3a–3c, it is also possible to have only fluid flow through output 32 at, for example, an angle (FIG. 3a) without an output 31. Other nozzle configurations are possible.

The source of optical radiation 13 can be either coherent (laser) or incoherent (incandescent or arc lamp). The term "light" as used herein shall mean radiation in a wavelength range of approximately 1 cm to 100 nm. The coherent sources for the proposed method are $CO_2$ or excimer lasers since most of the hard substances of abrasive particles, including these described above, have strong absorption in the far IR range (9–11 $\mu$m) and in UV range (the wavelength is shorter than 0.3 $\mu$m). The radiation of a mercury lamp may possibly be used in the UV range. Lasers based on yttrium-aluminum-garnet crystal doped by erbium or neodymium ions may be used as pulsed lasers. The radiation wavelengths for these lasers are 2.94 $\mu$m and 1.064 $\mu$m respectively. The energy of generated pulses is about 1 J, the duration of pulses may be varied from 50 to 5000 microseconds, the pulse repetition rate may be 25 Hz and the average power may be 15 W for an illustrative embodiment.

Pure water or a water solution of food dye can be used as the liquid. Where a neodymium laser is used, carbon particles with dimensions from 10 to 100 microns may be added to the food dye in water, this providing an absorption index value as high as $10^5$ cm$^{-1}$. If an Er-laser is used, water may be used as a shell, water having an absorption index on 2.94 $\mu$m, which is more than $10^6$ cm$^{-1}$. Saphire particles may be used as the abrasive particles for this embodiment.

A SEM photo of the crater formed in hard dental tissue (dentin) by YAG:ER laser radiation without application of abrasive particles and a similar photo of a crater formed with application of sapphire particles with diameter 12 $\mu$m in a water shell accelerated by a laser pulse with duration 200 $\mu$m and energy density 50 J/cm2 show that the application of the method and device described above results in a nearly twofold increase in the efficiency of processing of human hard tooth tissues.

In an alternative embodiment of the invention, abrasive particle delivery mechanism 19 is replaced by a solid body 40 mounted in an indexing mechanism 42 so as to be in the path of light radiation from radiation output 30. Body 40 may be in the form of a rod, ribbon, fiber, film or other suitable shape, and may for example be formed by presenting or pressing the abrasive particles to a solid body of the desired form. Conversely, the body 40 may be formed of abrasive particles embedded in a suitable binder, which binder may form a shell 9 for the particles 2, which shell is to be ablated or may form a transparent shell 10 (FIG. 1c). As ablation of body 14 under the influence of light radiation occurs, causing abrasive particles to be accelerated to material treatment zone 17, indexing mechanism 42 is operated under control of control unit 14 to maintain the end of body 40 in the path of light radiation to the processing zone.

Thus, while the invention has been particularly shown and described above with reference to preferred embodiments, and variations on the preferred embodiments have also been discussed, such variations and others may be made therein by one skilled in the art while still remaining within the spirit and scope of the invention, which is to be defined only by the appended claims.

What is claimed is:

1. A method for processing a material having an outer surface including:

distributing a substance containing abrasive particles in an area in front of at least a portion of said surface such that particles are present in said area during at least most of said processing; and irradiating both said substance and said portion of said surface with light selected to cause selective ablation of said substance sufficient to force said abrasive particles under a selected pulse against said portion of the surface.

2. A method as claimed in claim 1 wherein said substance is said abrasive particles, said particles being of size to be selectively ablated by said irradiation to force said particles against said surface.

3. A method as claimed in claim 2 wherein said particles have a size $d \gg k^{-1}(\lambda)$, where $k(\lambda)$ is the absorption characteristic of the particles at wavelength $\lambda$.

4. A method as claimed in claim 3 wherein $1\ \mu m < d < 1000\ \mu m$ and $10^5\ cm^{-1} > k > 10^2\ cm^{-1}$.

5. A method as claimed in claim 2 wherein said particles are distributed in said area by airflow.

6. A method as claimed in claim 1 wherein said substance includes the particles, each enclosed within a shell, said selective ablations being of said shell.

7. A method as claimed in claim 6 wherein each said shell has a thickness $\delta$ such that $\delta \gg k^{-1}(\lambda)$, where $k(\lambda)$ is the absorption characteristic of the particles at wavelength $\lambda$.

8. A method as claimed in claim 7 wherein $1\ \mu m < \delta < 1000\ \mu m$ and $10^5\ cm^{-1} > k > 10^2\ cm^{-1}$.

9. A method as claimed in claim 6 wherein said substance is a suspension of said particles in a liquid, said liquid being selectively ablated by said light.

10. A method as claimed in claim 9 wherein said distributing step distributes the suspension to the surface to cool the material, and wherein said irradiating step irradiates a small portion of said surface, particles being forced for the most part only against said small portion to cause processing thereof.

11. A method as claimed in claim 6 wherein said shell for each particle is substantially completely ablated by the irradiation thereof.

12. A method as claimed in claim 6 wherein said substance is a substantially solid body containing said particles, a component of said body being selectively ablated by said light, and wherein said distributing step includes the step performed throughout the processing of said material of maintaining a portion of said body between said light and said portion of the surface.

13. A method as claimed in claim 12 wherein said solid body is formed of a suspension of said particles in a substantially solid binder.

14. A method as claimed in claim 12 wherein said solid body is formed of said particles processed to adhere in a desired shape.

15. A method as claimed in claim 1 wherein said substance is distributed to said area for a duration $\tau$ and said light has an energy density E near said surface such that $\tau \ll d^2/4\alpha$ and $E \gg k^{-1}(\lambda)\rho Q$, where d is the size of the particles, $\alpha$ is the index of temperature conductivity for the particles, $k(\lambda)$ is the absorption characteristic of the particles at wavelength $\lambda$, $\rho$ is the density of the particles and Q is specific energy of transmission of particles from solid to gaseous state.

16. A method as claimed in claim 15 wherein $10^{-1}\ j/cm^2 < E < 10^4\ j/cm^2$.

17. A method as claimed in claim 1 wherein said irradiating is performed continuously.

18. A method as claimed in claim 1 wherein said irradiation is performed as a sequence of time spaced light pulses.

19. A method as claimed in claim 18 wherein said distributing of substance is by a series of distribution pulses.

20. A method as claimed in claim 19 wherein said distribution pulses are synchronous with said light pulses.

21. A method as claimed in claim 19 wherein a said distribution pulse occurs before each light pulse and the duration of said distribution pulses is less than the time between light pulses.

22. A method as claimed in claim 19 wherein said distribution pulses have a repetitions rate which is less than that for said light pulses.

23. Apparatus for processing a material having an outer surface including:

a mechanism selectively providing a substance containing abrasive particles in an area in front of at least a portion of said surface, said mechanism causing said particles to be present in said area during at least most of said processing;

a light source; and a system for selectively directing light from said source to irradiate both said substance and said portion of the surface, said source and said system being selected to cause selective ablation of said substance in response to the irradiation thereof sufficient to force said abrasive particles under a selected pulse against said portion of the surface.

24. Apparatus as claimed in claim 23 wherein said light source is one of a laser, an incandescent lamp and a flash lamp.

25. Apparatus as claimed in claim 23 wherein said system includes a control which operates said source in a selected pulse mode, and an optical system directing light from said source to a tip, said mechanism selectively providing said substance through said tip to said area, said tip being adapted to direct light through said area to said portion of the surface.

26. Apparatus as claimed in claim 25 wherein said mechanism provides the substance to said area as a series of distribution pulses.

27. Apparatus as claimed in claim 26 wherein said mechanism provides said distribution pulses synchronous with light pulses from said source.

28. Apparatus as claimed in claim 26 wherein a said distribution pulse occurs before each light pulse from said source and the duration of said distribution pulses is less than the time between light pulses.

29. Apparatus as claimed in claim 26 wherein said distribution pulses have a repetition rate which is less than the repetition rate for said selected pulse mode at which said source is operated.

30. Apparatus as claimed in claim 23 wherein said system includes a control which operates said source continuously, and an optical system directing light from said source to a tip, said mechanism selectively providing said substance through said tip to said area, said tip being adapted to direct light through said area to said portion of the surface.

31. Apparatus as claimed in claim 23 wherein said mechanism is operative to distribute said substance to said area for a duration $\tau$; and said source delivers light irradiation having an energy density E near said surface such that $\tau \ll d^2/4f\alpha$ and $E \gg k^{-1}(\lambda)\rho Q$, where d is the size of the particles, $\alpha$ is the index of temperature conductivity for the particles, $k(\lambda)$ is the absorption characteristic of the particles at wavelength $\lambda$, $\rho$ is the density of the particles and Q is specific energy of transmission of particles from solid to gaseous state.

32. Apparatus as claimed in claim 31 wherein $10^{-1}\ j/cm^2 < E < 10^4\ j/cm^2$.

33. Apparatus as claimed in claim 23 wherein said substance is said abrasive particles, said mechanism including a source of said particles, a carrier for delivering said particles to said area, and a control for operating on at least one of said carrier and said source to provide a controlled delivery of particles to said area, said particles being of a size to be selectively ablated by light irradiation directed thereat from said source.

34. Apparatus as claimed in claim 33 wherein said carrier is air delivered under pressure to an air pipe under control of a valve operated by said control, said particles being delivered from a source thereof to said air pipe to be carried therethrough by air to said area.

35. Apparatus as claimed in claim 23 wherein said mechanism includes a source of said particles in a liquid carrier, said substance being a suspension of said particles in said liquid, said liquid being selectively ablated by said light.

36. Apparatus as claimed in claim 35 wherein said mechanism is controlled to deliver said suspension to the surface to cool the material prior to said system applying light to the substance to ablate the liquid, forcing the particles for the most part only against a small portion of said surface irradiated by said light to cause processing of material at said portion.

37. Apparatus as claimed in claim 23 wherein said substance is in the form of a substantially solid body containing said particles, and including an indexing mechanism for supporting and maintaining said body in said area between said light and said portion of the surface.

38. Apparatus as claimed in claim 37 wherein said body is one of a suspension of said particles in a substantially solid binder, and said particles processed to adhere in a desired shape.

39. Apparatus as claimed in claim 23 said substance is sapphire particles suspended in water.

40. Apparatus as claimed in claim 39 wherein said light source is an Er:YAG laser.

41. Apparatus as claimed in claim 23 wherein said light source is one of a $CO_2$ laser and an excimer laser.

42. Apparatus as claimed in claim 23 wherein said light source is an Nd:YAG laser and wherein said particles are carbon particles.

43. Apparatus as claimed in claim 23 wherein the material being processed is biological tissue, and wherein said particles are of a biologically safe material.

44. Apparatus as claimed in claim 43 wherein said biologically safe material includes at least one of hydroxyapatite, carbon, silicon and ice.

* * * * *